United States Patent
Johann et al.

(10) Patent No.: US 7,488,857 B2
(45) Date of Patent: *Feb. 10, 2009

(54) METHOD FOR THE PRODUCTION OF BUTADIENE AND 1-BUTENE

(75) Inventors: Thorsten Johann, Limburgerhof (DE); Götz-Peter Schindler, Mannheim (DE); Andreas Brodhagen, Dannstadt-Schauernheim (DE); Sven Crone, Limburgerhof (DE); Regina Benfer, Altrip (DE); Marcus Sigl, Mannheim (DE); Mark Duda, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 126 days.

This patent is subject to a terminal disclaimer.

(21) Appl. No.: 10/584,783

(22) PCT Filed: Dec. 30, 2004

(86) PCT No.: PCT/EP2004/014835

§ 371 (c)(1),
(2), (4) Date: Jun. 28, 2006

(87) PCT Pub. No.: WO2005/063657

PCT Pub. Date: Jul. 14, 2005

(65) Prior Publication Data

US 2007/0161842 A1    Jul. 12, 2007

(30) Foreign Application Priority Data

Dec. 30, 2003 (DE) .............................. 103 61 823

(51) Int. Cl.
C07C 5/333    (2006.01)

(52) U.S. Cl. .................... 585/325; 585/616; 585/621; 585/628

(58) Field of Classification Search .............. 585/325, 585/616, 621, 628
See application file for complete search history.

(56) References Cited

U.S. PATENT DOCUMENTS

| | | | |
|---|---|---|---|
| 3,161,670 A * | 12/1964 | Adams et al. ............... 558/320 |
| 4,408,085 A | 10/1983 | Gottlieb et al. | |
| 4,558,168 A * | 12/1985 | Gussow et al. ............... 585/324 |
| 4,718,986 A | 1/1988 | Comiotto et al. | |
| 4,788,371 A | 11/1988 | Imai et al. | |
| 4,902,849 A | 2/1990 | Mckay et al. | |
| 4,996,387 A | 2/1991 | Gerhold et al. | |
| 4,996,849 A | 3/1991 | Burst et al. | |
| 5,087,780 A | 2/1992 | Arganbright | |
| 5,220,091 A | 6/1993 | Brinkmeyer et al. | |
| 5,389,342 A | 2/1995 | Savage et al. | |
| 5,430,220 A | 7/1995 | Khare et al. | |
| 5,877,369 A | 3/1999 | Wu et al. | |
| 5,955,640 A | 9/1999 | Paludetto et al. | |
| 6,414,209 B1 | 7/2002 | Herskowitz et al. | |
| 6,437,206 B1 | 8/2002 | Meyer et al. | |
| 6,670,303 B1 | 12/2003 | Heineke et al. | |
| 7,034,195 B2 | 4/2006 | Schindler et al. | |
| 2003/0220530 A1 * | 11/2003 | Boelt et al. ............... 585/648 |
| 2005/0119515 A1 | 6/2005 | Machhammer et al. | |
| 2005/0171311 A1 | 8/2005 | Schindler et al. | |

FOREIGN PATENT DOCUMENTS

| | | |
|---|---|---|
| DE | 199 37 105 | 2/2001 |
| DE | 199 37 106 | 2/2001 |
| DE | 199 37 107 | 2/2001 |
| DE | 102 11 275 | 9/2003 |
| EP | 0 117 146 | 8/1984 |
| EP | 0 129 900 | 1/1985 |
| EP | 0 751 106 | 1/1997 |
| EP | 0 992 284 | 4/2000 |
| GB | 628686 | 9/1949 |
| GB | 2 018 815 | 10/1979 |
| WO | WO-99/29420 | 6/1999 |
| WO | WO-99/46039 | 9/1999 |
| WO | WO-2004/007408 | 1/2004 |
| WO | WO-2004/063656 | 7/2005 |

OTHER PUBLICATIONS

Sannfilippo, et al. "Fluidized Bed Reactors For Parraffins Dehydrogenation", Chemical Engineering Science, vol. 47, No. 9-11, pp. 2313-2318, 1992.

* cited by examiner

*Primary Examiner*—Thuan Dinh Dang
(74) *Attorney, Agent, or Firm*—Connolly Bove Lodge & Hutz LLP

(57) ABSTRACT

The disclosure involves a process for the preparation of butadiene and 1-butene. The process includes at least a first catalytic dehydrogenation of n-butane to obtain a gas stream which is followed by at least a second oxidative dehydrogenation to form a second gas stream. The second gas stream is then subjected to distillation and isomeration steps to obtain butadiene and 1-butene.

6 Claims, No Drawings und 1-BUTENE

RELATED APPLICATIONS

This application is a national stage application (under 35 U.S.C. 371) of PCT/EP2004/014835 filed Dec. 30, 2004, which claims benefit to German application 103 61 823.6 filed Dec. 30, 2003.

The invention relates to a process for preparing butadiene and 1-butene.

Butadiene is an important basic chemical and is used, for example, to prepare synthetic rubbers (butadiene homopolymers, styrene-butadiene-rubber or nitrile rubber) or for preparing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Dimerization of butadiene also allows vinylcyclohexene to be generated, which can be dehydrogenated to styrene.

Just like butadiene, 1-butene is an important basic chemical. Starting from 1-butene, for example, n-valeraldehyde is obtained by the oxo process and hexene by metathesis.

Butadiene can be prepared by thermally cracking (steam-cracking) saturated hydrocarbons, in which case naphtha is typically used as the raw material. In the course of steam-cracking of naphtha, a hydrocarbon mixture of methane, ethane, ethene, acetylene, propane, propene, propyne, allene, butenes, butadiene, butynes, methylallene, $C_5$ and higher hydrocarbons is obtained.

A disadvantage of the generation of butadiene in the cracking process is that larger amounts of undesired coproducts are inevitably obtained.

It is an object of the invention to provide a process for preparing butadiene and 1-butene from n-butane, in which coproducts are obtained to a minimal extent.

The object is achieved by a process for preparing butadiene and 1-butene from n-butane having the steps of A) providing a feed gas stream a comprising n-butane;
B) feeding the feed gas stream a comprising n-butane into at least one first dehydrogenation zone and nonoxidatively catalytically dehydrogenating n-butane to obtain a product gas stream b comprising n-butane, 1-butene, 2-butene, butadiene, hydrogen, low-boiling secondary constituents and in some cases steam;
C) feeding the product gas stream b of the nonoxidative catalytic dehydrogenation and an oxygenous gas into at least one second dehydrogenation zone and oxidatively dehydrogenating 1-butene and 2-butene to obtain a product gas stream c comprising n-butane, 2-butene, butadiene, hydrogen, low-boiling secondary constituents and steam, said product gas stream c having a higher content of butadiene than the product gas stream b;
D) removing hydrogen, the low-boiling secondary constituents and steam to obtain a $C_4$ product gas stream d substantially consisting of n-butane, 2-butene and butadiene;
E) separating the $C_4$ product gas stream d into a stream e1 consisting substantially of n-butane and 2-butene and a product of value stream e2 consisting substantially of butadiene by extractive distillation;
F) feeding the stream e1 consisting substantially of n-butane and 2-butene and a cycle stream g comprising 1-butene and 2-butene into a distillation zone and separating into a 1-butene-rich product of value stream f1, a recycle stream f2 comprising 2-butene and n-butane and a stream f3 comprising 2-butene, and recycling the recycle stream f2 into the first dehydrogenation zone;
G) feeding the stream f3 comprising 2-butene into an isomerization zone and isomerizing 2-butene to 1-butene to obtain a cycle stream g comprising 1-butene and 2-butene, and recycling the cycle gas stream g into the distillation zone.

The process according to the invention features particularly effective utilization of the raw materials. Thus, losses of the n-butane raw material are minimized by recycling unconverted n-butane into the dehydrogenation. The coupling of nonoxidative catalytic dehydrogenation and oxidative dehydrogenation achieves a high butadiene yield. The isomerization of 2-butene to 1-butene also yields 1-butene as the product of value.

In a first process part, A, a feed gas stream a comprising n-butane is provided. Typically, the starting raw materials are n-butane-rich gas mixtures such as liquefied petroleum gas (LPG). LPG comprises substantially saturated $C_2$-$C_5$ hydrocarbons. In addition, it also contains methane and traces of $C_6^+$ hydrocarbons. The composition of LPG may vary markedly. Advantageously, the LPG used contains at least 10% by weight of butanes.

Alternatively, a refined $C_4$ stream from crackers or refineries may be used.

In one variant of the process according to the invention, the provision of the dehydrogenation feed gas stream comprising n-butane comprises the steps of (A1) providing a liquefied petroleum gas (LPG) stream,
(A2) removing propane and any methane, ethane and $C_5^+$ hydrocarbons (mainly pentanes, additionally hexanes, heptanes, benzene, toluene) from the LPG stream to obtain a stream comprising butanes (n-butane and isobutane),
(A3) removing isobutane from the stream containing butanes to obtain the feed gas stream comprising n-butane, and, if desired, isomerizing the isobutane removed to give an n-butane/isobutane mixture and recycling the n-butane/isobutane mixture into the isobutane removal.

Propane and any methane, ethane and $C_5^+$ hydrocarbons are removed, for example, in one or more customary rectification columns. For example, in a first column, low boilers (methane, ethane, propane) may be removed overhead and, in a second column, high boilers ($C_5^+$ hydrocarbons) may be removed at the bottom of the column. A stream comprising butanes (n-butane and isobutane) is obtained, from which isobutane is removed, for example in a customary rectification column. The remaining stream comprising n-butane is used as the feed gas stream for the downstream butane dehydrogenation.

The isobutane stream removed is preferably subjected to isomerization. To this end, the stream comprising isobutane is fed into an isomerization reactor. The isomerization of isobutane to n-butane may be carried out as described in GB-A 2 018 815. An n-butane/isobutane mixture is obtained and is fed into the n-butane/isobutane separating column.

The isobutane stream removed may also be sent to a further use, for example for preparing methacrylic acid, polyisobutene or methyl tert-butyl ether.

In one process part, B, the feed gas stream comprising n-butane is fed into a dehydrogenation zone and subjected to a nonoxidative catalytic dehydrogenation. In this dehydrogenation, n-butane is partly dehydrogenated in a dehydrogenation reactor over a dehydrogenating catalyst to give 1-butene and 2-butene, although butadiene is also formed. In addition, hydrogen and small amounts of methane, ethane, ethene, propane and propene are obtained. Depending on the method of the dehydrogenation, carbon oxides ($CO$, $CO_2$), water and nitrogen may also be present in the product gas mixture of the nonoxidative catalytic n-butane dehydrogenation. Unconverted n-butane is additionally present in the product gas mixture.

The nonoxidative catalytic n-butane dehydrogenation may be carried out with or without oxygenous gas as a cofeed.

One feature of the nonoxidative method compared to an oxidative method is the presence of hydrogen in the effluent gas. In the oxidative dehydrogenation, free hydrogen is not formed in substantial amounts.

The nonoxidative catalytic n-butane dehydrogenation may in principle be carried out in any reactor types and methods disclosed by the prior art. A comparatively comprehensive description of dehydrogenation processes suitable in accordance with the invention is also contained in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable reactor form is a fixed bed tubular or tube bundle reactor. In these reactors, the catalyst (dehydrogenation catalyst and, when working with oxygen as the cofeed, optionally a special oxidation catalyst) is disposed as a fixed bed in a reaction tube or in a bundle of reaction tubes. The reaction tubes are customarily heated indirectly by the combustion of a gas, for example a hydrocarbon such as methane, in the space surrounding the reaction tubes. It is favorable to apply this indirect form of heating only to about the first 20 to 30% of the length of the fixed bed and to heat the remaining bed length to the required reaction temperature by the radiant heat released in the course of indirect heating. Customary reaction tube internal diameters are from about 10 to 15 cm. A typical dehydrogenation tube bundle reactor comprises from about 300 to 1000 reaction tubes. The internal temperature in the reaction tubes typically varies in the range from 300 to 1200° C., preferably in the range from 500 to 1000° C. The working pressure is customarily from 0.5 to 8 bar, frequently from 1 to 2 bar, when a small steam dilution is used (similar to the Linde process for propane dehydrogenation), or else from 3 to 8 bar when using a high steam dilution (similar to the steam active reforming process (STAR process) for dehydrogenating propane or butane of Phillips Petroleum Co., see U.S. Pat. Nos. 4,902,849, 4,996,387 and 5,389,342). Typical gas hourly space velocities (GHSV) are from 500 to 2000 $h^{-1}$, based on the hydrocarbon used. The catalyst geometry may, for example, be spherical or cylindrical (hollow or solid).

The nonoxidative catalytic n-butane dehydrogenation may also be carried out using the heterogeneous catalysis in a fluidized bed, as described in Chem. Eng. Sci. 1992 b, 47 (9-11) 2313. Appropriately, two fluidized beds are operated in parallel, of which one is generally in the process of regeneration. The working pressure is typically from 1 to 2 bar, the dehydrogenation temperature generally from 550 to 600° C. The heat required for the dehydrogenation is introduced into the reaction system by preheating the dehydrogenation catalyst to the reaction temperature. The admixing of an oxygenous cofeed allows the preheater to be dispensed with and the required heat to be generated directly in the reactor system by combustion of hydrogen and/or hydrocarbons in the presence of oxygen. Optionally, a hydrogen-containing cofeed may additionally be admixed.

The nonoxidative catalytic n-butane dehydrogenation may be carried out in a tray reactor with or without oxygenous gas as a cofeed. This reactor comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by the reaction gas. In general, such a tray reactor is operated using a fixed catalyst bed. In the simplest case, the fixed catalyst beds are disposed axially in a shaft furnace reactor or in the annular gaps of concentric cylindrical grids. A shaft furnace reactor corresponds to one tray. Carrying out the dehydrogenation in a single shaft furnace reactor corresponds to a preferred embodiment, in which it is possible to work with oxygenous cofeed. In a further preferred embodiment, the dehydrogenation is carried out in a tray reactor having 3 catalyst beds. In a method without oxygenous gas as cofeed, the reaction gas mixture is subjected to intermediate heating in the tray reactor on its way from one catalyst bed to the next catalyst bed, for example by passing it over heat exchanger plates heated by hot gases or by passing it through tubes heated by hot combustion gases.

In a preferred embodiment of the process according to the invention, the nonoxidative catalytic n-butane dehydrogenation is carried out autothermally. To this end, the reaction gas mixture of the n-butane dehydrogenation is additionally admixed with oxygen in at least one reaction zone and the hydrogen and/or hydrocarbon present in the reaction gas mixture is at least partially combusted, which directly generates in the reaction gas mixture at least a portion of the heat required for dehydrogenation in the at least one reaction zone.

In general, the amount of oxygenous gas added to the reaction gas mixture is selected in such a manner that the amount of heat required for the dehydrogenation of n-butane is generated by the combustion of the hydrogen present in the reaction gas mixture and any hydrocarbons present in the reaction gas mixture and/or carbon present in the form of coke. In general, the total amount of oxygen supplied, based on the total amount of butane, is from 0.001 to 0.5 mol/mol, preferably from 0.005 to 0.2 mol/mol, more preferably from 0.05 to 0.2 mol/mol. Oxygen may be used either as pure oxygen or as an oxygenous gas in the mixture with inert gases, for example in the form of air. The inert gases and the gases resulting from the combustion generally provide additional dilution and therefore promote the heterogeneously catalyzed dehydrogenation.

The hydrogen combusted to generate heat is the hydrogen formed in the catalytic n-butane dehydrogenation and also any hydrogen additionally added to the reaction gas mixture as hydrogenous gas. The amount of hydrogen present should preferably be such that the $H_2/O_2$ molar ratio in the reaction gas mixture immediately after the oxygen is fed in is from 1 to 10 mol/mol, preferably from 2 to 5 mol/mol. In multistage reactors, this applies to every intermediate feed of oxygenous and any hydrogenous gas.

The hydrogen is combusted catalytically. The dehydrogenation catalyst used generally also catalyzes the combustion of the hydrocarbons and of hydrogen with oxygen, so that in principle no specialized oxidation catalyst is required apart from it. In one embodiment, operation is effected in the presence of one or more oxidation catalysts which selectively catalyze the combustion of hydrogen with oxygen to water in the presence of hydrocarbons.

The combustion of these hydrocarbons with oxygen to give $CO$, $CO_2$ and water therefore proceeds only to a minor extent. The dehydrogenation catalyst and the oxidation catalyst are preferably present in different reaction zones.

When the reaction is carried out in more than one stage, the oxidation catalyst may be present only in one, in more than one or in all reaction zones.

Preference is given to disposing the catalyst which selectively catalyzes the oxidation of hydrogen at the points where there are higher partial oxygen pressures than at other points in the reactor, in particular near the feed point for the oxygenous gas. The oxygenous gas and/or hydrogenous gas may be fed in at one or more points in the reactor.

In one embodiment of the process according to the invention, there is intermediate feeding of oxygenous gas and of hydrogenous gas upstream of each tray of a tray reactor. In a further embodiment of the process according to the invention, oxygenous gas and hydrogenous gas are fed in upstream of each tray except the first tray. In one embodiment, a layer of a specialized oxidation catalyst is present downstream of every feed point, followed by a layer of the dehydrogenation catalyst. In a further embodiment, no specialized oxidation catalyst is present. The dehydrogenation temperature is generally from 400 to 1100° C., the pressure in the last catalyst bed of the tray reactor is generally from 0.2 to 5 bar, preferably from 1 to 3 bar. The GHSV is generally from 500 to 2000 $h^{-1}$, and in high-load operation, even up to 100 000 $h^{-1}$, preferably from 4000 to 16 000 $h^{-1}$.

A preferred catalyst which selectively catalyzes the combustion of hydrogen comprises oxides and/or phosphates selected from the group consisting of the oxides and/or phosphates or germanium, tin, lead, arsenic, antimony and bismuth. A further preferred catalyst which catalyzes the combustion of hydrogen comprises a noble metal of transition group VIII and/or I of the periodic table.

The dehydrogenation catalysts used generally comprise a support and an active composition. The support generally consists of a heat-resistant oxide or mixed oxide. The dehydrogenation catalysts preferably comprise a metal oxide selected from the group consisting of zirconium oxide, zinc oxide, aluminum oxide, silicon dioxide, titanium dioxide, magnesium oxide, lanthanum oxide, cerium oxide and mixtures thereof, as a support. The mixtures may be physical mixtures or else chemical mixed phases such as magnesium aluminum oxide or zinc aluminum oxide mixed oxides. Preferred supports are zirconium dioxide and/or silicon dioxide, and particular preference is given to mixtures of zirconium dioxide and silicon dioxide.

The active composition of the dehydrogenation catalysts generally comprises one or more elements of transition group VIII of the periodic table, preferably platinum and/or palladium, more preferably platinum. Furthermore, the dehydrogenation catalysts may comprise one or more elements of main group I and/or II of the periodic table, preferably potassium and/or cesium. The dehydrogenation catalysts may further comprise one or more elements of transition group III of the periodic table including the lanthanides and actinides, preferably lanthanum and/or cerium. Finally, the dehydrogenation catalysts may comprise one or more elements of main group III and/or IV of the periodic table, preferably one or more elements selected from the group consisting of boron, gallium, silicon, germanium, tin and lead, more preferably tin.

In a preferred embodiment, the dehydrogenation catalyst comprises at least one element of transition group VIII, at least one element of main group I and/or II, at least one element of main group III and/or IV and at least one element of transition group III including the lanthanides and actinides.

For example, all dehydrogenation catalysts which are disclosed by WO 99/46039, U.S. Pat. No. 4,788,371, EP-A 705 136, WO 99/29420, U.S. Pat. Nos. 5,220,091, 5,430,220, 5,877,369, EP 0 117 146, DE-A 199 37 106, DE-A 199 37 105 and DE-A 199 37 107 may be used according to the invention. Particularly preferred catalysts for the above-described variants of autothermal n-butane dehydrogenation are the catalysts according to examples 1, 2, 3 and 4 of DE-A 199 37 107.

Preference is given to carrying out the n-butane dehydrogenation in the presence of steam. The added steam serves as a heat carrier and supports the gasification of organic deposits on the catalysts, which counteracts carbonization of the catalysts and increases the onstream time of the catalysts. The organic deposits are converted to carbon monoxide, carbon dioxide and in some cases water.

The dehydrogenation catalyst may be regenerated in a manner known per se. For instance, steam may be added to the reaction gas mixture or an oxygenous gas may be passed from time to time over the catalyst bed at elevated temperature and the deposited carbon burnt off. Dilution with steam shifts the equilibrium toward the products of dehydrogenation. After the regeneration, the catalyst is optionally reduced with a hydrogenous gas.

The nonoxidative catalytic n-butane dehydrogenation provides a gas mixture which, in addition to butadiene, 1-butene, 2-butene and unconverted n-butane, comprises secondary constituents. Customary secondary constituents include hydrogen, steam, nitrogen, CO and $CO_2$, methane, ethane, ethene, propane and propene. The composition of the gas mixture leaving the first dehydrogenation zone may be highly variable depending on the dehydrogenation method. For instance, in the preferred autothermal dehydrogenation with feeding in of oxygen and additional hydrogen, the product gas mixture comprises a comparatively high content of steam and carbon oxides. In methods without feeding in of oxygen, the product gas mixture of the nonoxidative dehydrogenation has a comparatively high hydrogen content.

The product gas stream of the nonoxidative autothermal n-butane dehydrogenation typically contains from 0.1 to 15% by volume of butadiene, from 1 to 15% by volume of 1-butene, from 1 to 25% by volume of 2-butene (cis/trans-2-butene), from 20 to 70% by volume of n-butane, from 1 to 70% by volume of steam, from 0 to 10% by volume of low-boiling hydrocarbons (methane, ethane, ethene, propane and propene), from 0.1 to 40% by volume of hydrogen, from 0 to 70% by volume of nitrogen and from 0 to 5% by volume of carbon oxides.

The product gas stream b leaving the first dehydrogenation zone is preferably separated into two substreams, of which only one of the two substreams is subjected to the further process parts C to G and the second substream may be recycled into the first dehydrogenation zone. An appropriate procedure is described in DE-A 102 11 275. However, the entire product gas stream b of the nonoxidative catalytic n-butane dehydrogenation may also be subjected to the further process parts C to G.

According to the invention, the nonoxidative catalytic dehydrogenation is followed downstream by an oxidative dehydrogenation (oxydehydrogenation) as process part C. This substantially dehydrogenates 1-butene and 2-butene to 1,3-butadiene, and 1-butene is generally virtually fully depleted.

This may in principle be carried out in all reactor types and methods disclosed by the prior art, for example in a fluidized bed, in a tray furnace, in a fixed bed tubular or tube bundle reactor, or in a plate heat exchanger reactor. The latter is preferably used in the process according to the invention. To carry out the oxidative dehydrogenation, a gas mixture is required which has a molar oxygen: n-butenes ratio of at least 0.5. Preference is given to working at an oxygen:n-butenes ratio of from 0.55 to 50. To attain this value, the product gas mixture stemming from the nonoxidative catalytic dehydrogenation is mixed with oxygen or an oxygenous gas, for example air. The resulting oxygenous gas mixture is then fed to the oxydehydrogenation.

The catalysts which are particularly suitable for the oxydehydrogenation are generally based on an Mo—Bi—O multimetal oxide system which generally additionally comprises iron. In general, the catalyst system also comprises additional components from groups 1 to 15 of the periodic table, for example potassium, magnesium, zirconium, chromium, nickel, cobalt, cadmium, tin, lead, germanium, lanthanum, manganese, tungsten, phosphorus, cerium, aluminum or silicon.

Suitable catalysts and their preparation are described, for example, in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$) and DE-A 24 40 329 ($Mo_{12}BiCo_{4.5}Ni_{2.5}Cr_3P_{0.5}K_{0.1}O_x$).

The stoichiometry of the active composition of a multitude of multimetal oxide catalysts suitable for the oxydehydrogenation can be encompassed under the general formula (I)

$$Mo_{12}Bi_aFe_bCo_cNi_dCr_eX^1{}_fK_gO_x \qquad (I)$$

where the variables are defined as follows:

| | |
|---|---|
| $X^1 =$ | W, Sn, Mn, La, Ce, Ge, Ti, Zr, Hf, Nb, P, Si, Sb, Al, Cd and/or Mg; |
| $a =$ | from 0.5 to 5, preferably from 0.5 to 2; |
| $b =$ | from 0 to 5, preferably from 2 to 4; |
| $c =$ | from 0 to 10, preferably from 3 to 10; |
| $d =$ | from 0 to 10; |
| $e =$ | from 0 to 10, preferably from 0.1 to 4; |
| $f =$ | from 0 to 5, preferably from 0.1 to 2; |
| $g =$ | from 0 to 2, preferably from 0.01 to 1; and |
| $x =$ | a number which is determined by the valency and frequency of the elements in (I) other than oxygen. |

In the process according to the invention, preference is given to using an Mo—Bi—Fe—O multimetal oxide system for the oxydehydrogenation, and particular preference is given to an Mo—Bi—Fe—Cr—O or Mo—Bi—Fe—Zr—O metal oxide system. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Mo_{12}BiFe_3Co_{4.5}Ni_{2.5}Sn_{0.5}K_{0.1}O_x$), and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$). The preparation and characterization of the catalysts mentioned are described comprehensively in the documents cited.

The oxydehydrogenation catalyst is generally used as shaped bodies having an average size of over 2 mm. Owing to the pressure drop to be observed when performing the process, smaller shaped bodies are generally unsuitable. Examples of useful shaped bodies include tablets, cylinders, hollow cylinders, rings, spheres, strands, wagon wheels or extrudates. Special shapes, for example "trilobes" and "tristars" (see EP-A-0 593 646) or shaped bodies having at least one notch on the exterior (see U.S. Pat. No. 5,168,090) are likewise possible.

In general, the catalyst used may be used as an unsupported catalyst. In this case, the entire shaped catalyst body consists of the active composition, including any auxiliary, such as graphite or pore former and also further components. In particular, it has proven advantageous to use the Mo—Bi—Fe—O catalyst preferably used for the oxydehydrogenation of n-butenes to butadiene as an unsupported catalyst. Furthermore, it is possible to apply the active compositions of the catalysts to a support, for example an inorganic, oxidic shaped body. Such catalysts are generally referred to as coated catalysts.

The oxydehydrogenation is generally carried out at a temperature of from 220 to 490° C. and preferably from 250 to 450° C. A reactor entrance pressure is selected which is sufficient to overcome the flow resistances in the plant and the subsequent workup. This reactor entrance pressure is generally from 0.005 to 1 MPa above atmospheric pressure, preferably from 0.01 to 0.5 MPa above atmospheric pressure. By its nature, the gas pressure applied in the entrance region of the reactor substantially falls over the entire catalyst bed.

The coupling of the nonoxidative catalytic, preferably autothermal, dehydrogenation with the oxidative dehydrogenation of the n-butenes formed provides a very much higher yield of butadiene based on n-butane used. The nonoxidative dehydrogenation can also be operated in a gentler manner. Comparable butadiene yields would only be achievable with an exclusively nonoxidative dehydrogenation at the cost of distinctly reduced selectivities. Exclusively oxidative dehydrogenation only achieves low n-butane conversions.

In addition to butadiene and unconverted n-butane, the product gas stream c leaving the oxidative dehydrogenation comprises 2-butene and steam. As secondary constituents it generally comprises carbon monoxide, carbon dioxide, oxygen, nitrogen, methane, ethane, ethene, propane and propene, with or without hydrogen and also oxygenous hydrocarbons, known as oxygenates. In general, it only comprises very small proportions of 1-butene.

In general, the product gas stream c leaving the oxidative dehydrogenation has from 1 to 40% by volume of butadiene, from 20 to 80% by volume of n-butane, from 0.5 to 40% by volume of 2-butene, from 0 to 40% by volume of 1-butene, from 0 to 70% by volume of steam, from 0 to 10% by volume of low-boiling hydrocarbons (methane, ethane, ethene, propane and propene), from 0.1 to 40% by volume of hydrogen, from 0 to 70% by volume of nitrogen, from 0 to 10% by volume of carbon oxides and from 0 to 10% by volume of oxygenates. Oxygenates may be, for example, furan, acetic acid, maleic anhydride, formic acid or butyraldehyde.

In one process part, D, low-boiling secondary constituents other than the $C_4$ hydrocarbons (n-butane, isobutane, 1-butene, cis-/trans-2-butene, isobutene, butadiene) are at least partly, but preferentially substantially completely, removed from the product gas stream of the n-butane dehydrogenation to obtain a $C_4$ product gas stream d.

In one embodiment of the process according to the invention, water is initially removed from the product gas stream c in process part D. Water may be removed, for example, by condensing out by cooling and/or compressing the product gas stream c, and may be carried out in one or more cooling and/or compression stages.

The low-boiling secondary constituents may be removed from the product gas stream by customary separation processes such as distillation, rectification, membrane processes, absorption or adsorption.

To remove the hydrogen present in the product gas stream c, the product gas mixture, if appropriate on completion of cooling, is passed through a membrane, generally configured as a tube, which is permeable only to molecular hydrogen, for example in an indirect heat exchanger. The thus removed molecular hydrogen may, if required, be used at least partly in the dehydrogenation or else sent to another utilization, for example for generating electrical energy in fuel cells.

The carbon dioxide present in the product gas stream c may be removed by $CO_2$ gas scrubbing. The carbon dioxide gas scrubbing may be preceded upstream by a separate combustion stage in which carbon monoxide is selectively oxidized to carbon dioxide.

In a preferred embodiment of the process according to the invention, the uncondensable or low-boiling gas constituents such as hydrogen, oxygen, carbon oxides, the low-boiling hydrocarbons (methane, ethane, ethene, propane, propene) and any nitrogen are removed by means of a high-boiling absorbent in an absorption/desorption cycle to obtain a $C_4$ product gas stream c which consists substantially of the $C_4$ hydrocarbons. In general, at least 80% by volume, preferably at least 90% by volume, more preferably at least 95% by volume, of the $C_4$ product gas stream c consists of the $C_4$ hydrocarbons. The stream d consists substantially of n-butane, 2-butene and butadiene.

To this end, in an absorption stage, the product gas stream c, after preceding water removal, is contacted with an inert absorbent and the $C_4$ hydrocarbons are absorbed in the inert absorbent to obtain absorbent laden with $C_4$ hydrocarbons and an offgas comprising the remaining gas constituents. In a desorption stage, the $C_4$ hydrocarbons are released again from the absorbent.

Inert absorbents used in the absorption stage are generally high-boiling nonpolar solvents in which the $C_4$ hydrocarbon mixture to be removed has a distinctly higher solubility than the remaining gas constituents to be removed. The absorption may be effected by simply passing the product gas stream c through the absorbent. However, it may also be effected in columns or in rotary absorbers. Operation may be effected in cocurrent, countercurrent or crosscurrent. Examples of suitable absorption columns include tray columns having bubble-cap, centrifugal and/or sieve trays, columns having structured packings, for example sheet metal packings having a specific surface area of from 100 to 1000 $m^2/m^3$ such as Mellapak® 250 Y, and randomly packed columns. However, useful absorption columns also include trickle and spray towers, graphite block absorbers, surface absorbers such as thick-film and thin-film absorbers and also rotary columns, plate scrubbers, cross-spray scrubbers and rotary scrubbers.

Suitable absorbents are comparatively nonpolar organic solvents, for example aliphatic $C_8$- to $C_{18}$-alkenes, or aromatic hydrocarbons such as the middle oil fractions from paraffin distillation, or ethers having bulky groups, or mixtures of these solvents, to each of which a polar solvent such as 1,2-dimethyl phthalate may be added. Further suitable absorbents include esters of benzoic acid and phthalic acid with straight-chain $C_1$-$C_8$-alkanols, such as n-butyl benzoate, methyl benzoate, ethyl benzoate, dimethyl phthalate, diethyl phthalate, and also heat carrier oils, such as biphenyl and diphenyl ether, their chlorine derivatives and also triarylalkenes. A useful absorbent is a mixture of biphenyl and diphenyl ether, preferably in the azeotropic composition, for example the commercially available Diphyl®. Frequently, this solvent mixture contains dimethyl phthalate in an amount of 0.1 to 25% by weight. Further suitable absorbents are octanes, nonanes, decanes, undecanes, dodecanes, tridecanes, tetradecanes, pentadecanes, hexadecanes, heptadecanes and octadecanes, or fractions obtained from refinery streams which have the linear alkanes mentioned as main components.

For desorption of the $C_4$ hydrocarbons, the laden absorbent is heated and/or decompressed to a lower pressure. Alternatively, desorption may also be effected by stripping or in a combination of decompression, heating and stripping in one or more process steps. The absorbent regenerated in the desorption stage is recycled into the absorption stage.

In one process step, the desorption step is carried out by decompressing and/or heating the laden desorbent.

The removal D is generally not entirely complete, so that, depending on the type of removal, small amounts or even only traces of the further gas constituents, especially of the low-boiling hydrocarbons, may still be present in the $C_4$ product gas stream.

The volume flow reduction brought about by the removal D also deburdens the downstream process steps.

The $C_4$ product gas stream d consisting substantially of n-butane, 2-butene and butadiene contains generally from 20 to 80% by volume of butadiene, from 20 to 80% by volume of n-butane, from 0 to 50% by volume of 2-butene and from 0 to 20% by volume of 1-butene.

In one process part, E, the $C_4$ product gas stream d is separated by means of extractive distillation into a stream e1 consisting substantially of n-butane and 2-butene and a product of value stream e2 consisting substantially of butadiene.

The extractive distillation may be carried out as described in Erdöl und Kohle-Erdgas-Petrochemie [Mineral Oil and Coal-Natural Gas-Petrochemistry], volume 34 (8), pages 343-346 or Ullmanns Enzyklopädie der Technischen Chemie, volume 9, 4th edition 1975, pages 1 to 18.

To this end, the $C_4$ product gas stream d is contacted in an extraction zone with an extractant, preferably an N-methylpyrrolidone (NMP)/water mixture. The extraction zone is generally configured in the form of a wash column which comprises trays, random packings or structured packings as internals. It generally has from 30 to 70 theoretical plates, so that sufficiently good separating action is achieved. The wash column preferably has a backwash zone in the top of the column. This backwash zone serves to recycle the extractant present in the gas phase by means of a liquid hydrocarbon reflux, for which the top fraction is condensed beforehand. Typical temperatures at the top of the column are between 30 and 60° C. The mass ratio of extractant to $C_4$ product gas stream d in the feed of the extraction zone is generally from 10:1 to 20:1.

Suitable extractants are butyrolactone, nitriles such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP). In general, alkyl-substituted lower aliphatic amides or N-alkyl-substituted cyclic arnides are used. Particularly advantageous are dimethylformamide, acetonitrile, furfural and especially NMP.

However, it is also possible to use mixtures of these extractants with one another, for example of NMP and acetonitrile, mixtures of these extractants with cosolvents and/or tert-butyl ethers, e.g. methyl tert-butyl ether, ethyl tert-butyl ether, propyl tert-butyl ether, n- or isobutyl tert-butyl ether. Particularly suitable is NMP, preferably in aqueous solution, preferably with from 0 to 20% by weight of water, more preferably with from 7 to 10% by weight of water, in particular with 8.3% by weight of water.

In the extraction zone, a gaseous stream e1 consisting substantially of n-butane and 2-butene and an extraction solution comprising butadiene are formed. In general, the stream e1 consisting substantially of n-butane and 2-butene ccontains from 50 to 100% by volume on n-butane, from 0 to 50% by volume of 2-butene and from 0 to 3% by volume of further constituents such as isobutane, isobutene, propane, propene and $C_5^+$ hydrocarbons.

The extraction solution is transferred into a desorption zone having reduced pressure and/or elevated temperature compared to the extraction zone, and the butadiene is desorbed from the extraction solution. The desorption zone may be configured, for example, in the form of a wash column which has from 5 to 15, preferably from 8 to 10, theoretical plates, and a backwash zone having, for example, 4 theoretical plates. This backwash zone serves to recover the extractant present in the gas phase by means of liquid hydrocarbon reflux, for which the top fraction is condensed beforehand. The internals provided are structured packings, trays or random packings. The pressure at the top of the column is, for example, 1.5 bar. The temperature in the bottom of the column is, for example, from 130 to 150° C.

The product of value stream e2 obtained at the top of the column generally contains from 90 to 100% by volume of butadiene, from 0 to 10% by volume of 2-butene and from 0 to 10% by volume of n-butane and 1-butene.

In one process part F, the stream e1 consisting substantially of n-butane and 2-butene and a cycle stream g which comprises 1-butene and 2-butene and which is obtained by isomerizing 2-butene in a process part, G, disposed downstream are fed into a distillation zone. There, a product of value stream f1 consisting substantially of 1-butene is obtained, a recycle stream f2 comprising 2-butene and n-butane and a stream f3 comprising 2-butene are obtained. The recycle stream f2 is recycled into the first dehydrogenation zone (nonoxidative catalytic dehydrogenation). The product of value stream f1 is discharged from the process. The stream f3 is fed to the isomerization to obtain further 1-butene.

The distillation zone generally consists of a distillation column having generally from 30 to 80, preferably from 40 to 75, theoretical plates. Suitable are, for example, bubble-cap tray columns, columns having random packings or structured packings, or dividing wall columns. The reflux ratio is generally from 10 to 50. The distillation is generally carried out at a pressure of from 5 to 20 bar.

In the upper section of the column, preferably at the top of the column, a 1-butene-rich stream f1 is drawn off. The proportion of 1-butene, based on the sum of 1-butene and 2-butenes, is greater than the corresponding proportion in the column feed e1. In the stream f1, the proportion of 1-butene, based on the sum of 1-butene and 2-butenes, is generally at least 90%, preferably at least 95%.

In the lower section of the column, preferably in the lower fifth of the column, more preferably at the bottom of the column up to a maximum of 5 theoretical plates above the bottom of the column, a cycle stream comprising 2-butene is drawn off for isomerization (stream f3). Typically, the proportion of 1-butene, based on the sum of 1-butene and 2-butenes, in the stream f3 is less than 20%, preferably less than 15%. A purge gas stream may be removed from the cycle stream f3 in order to prevent the accumulation of high boilers. The purge gas stream may be recycled into the dehydrogenation zone as a recycle stream f2. The recycle stream f2 may also be obtained separately from stream f3 as a bottom draw stream. The proportion of 1-butene, based on the sum of 1-butene and 2-butene, in the bottom draw stream is generally less than 15%, preferably less than 10%.

In one process part, G, the stream f3 consisting substantially of 2-butene is fed into an isomerization zone and the isomerization of 2-butene to 1-butene is carried out. The stream f3 consisting substantially of 2-butene is passed over an isomerization catalyst. Suitable isomerization catalysts are basic catalysts or catalysts based on zeolite. In addition, the isomerization may also be effected under hydrogenating conditions over noble metal catalysts.

Suitable catalysts are alkaline earth metal oxides on alumina, as described in EP-A 0 718 036, mixed alumina/silica supports which are doped with oxides of the alkaline earth metals, boron group metals, lanthanides or elements of the iron group, as described in U.S. Pat. No. 4,814,542, or gamma-alumina coated with alkali metals, as described in JP 51/108691. Also suitable is manganese oxide on alumina, as described in U.S. Pat. No. 4,289,919, magnesium oxide, alkali metal oxide and zirconium oxide dispersed on an alumina support, as described in EP-A 0 234 498 and also alumina catalysts which additionally comprise sodium oxide and silicon dioxide, as described in U.S. Pat. No. 4,229,610.

Suitable zeolite-based catalysts are described in EP-A 0 129 899. Also suitable are molecular sieves which have been exchanged with alkali metals or alkaline earth metals, as described in U.S. Pat. No. 3,475,511, aluminosilicates, as described in U.S. Pat. No. 4,749,819 and also zeolites in alkali metal and alkaline earth metal form, as described in U.S. Pat. No. 4,992,613, and those based on crystalline borosilicates, as described in U.S. Pat. No. 4,499,326.

The catalysts are typically used in a fixed bed, fluidized bed or moving bed. For the isomerization, preference is given to a continuous-flow fixed bed reactor. Suitable reactors are tubular reactors, tube bundle reactors, coil reactors or helical reactors. The isomerization temperature is generally from 100 to 700° C., preferably from 200 to 500° C. The pressure is generally from 1 to 30 bar, preferably from 3 to 20 bar.

A cycle gas stream g is obtained whose proportion of 1-butene, based on the sum of 1-butene and 2-butenes, is between 10 and 30%, preferably between 15 and 25%. When the proportion of 1-butene, based on the sum of 1-butene and 2-butenes, in the reactor feed (stream f3) is compared with the corresponding proportion in the reactor effluent (stream g), the latter is larger than the former by a factor of from 1.3 to 25. The cycle gas stream g is fed into the distillation zone together with the stream e1 consisting substantially of n-butane and 2-butene. From the cycle stream g, a purge gas stream may be removed.

EXAMPLE

A feed gas stream (4) comprising n-butane, said stream being obtained by combining a fresh gas stream (1) and a recycle stream (12), is fed to the first, autothermally operated, nonoxidative catalytic n-butane dehydrogenation stage (BDH). To provide the heat required for the endothermic dehydrogenation, hydrogen is combusted selectively and is fed together with the combustion air as stream (2). In order to counteract carbonization of the catalyst and prolong the onstream time of the catalyst, steam (3) is also added. A dehydrogenation gas mixture (5) is obtained, which is cooled after leaving the BDH and fed to the second, oxidative, n-butane dehydrogenation stage (ODH). Also fed to the ODH is an air stream (6). For BDH and ODH, based on experimental results, the degrees of conversion and selectivities reproduced in Table 1 were assumed.

TABLE 1

| Reaction stage | Conversion [%] | Selectivity [%] |
|---|---|---|
| Autothermal dehydrogenation (BDH) | 50.5 (n-butane) | 98.4 (to butenes/butadiene) |
| Oxidative dehydrogenation (ODH) | 100.0 (1-butene) 92.7 (2-butene) | 95.0 (to butadiene) |

The exit gas (7) of the ODH is compressed with intermediate cooling in several stages. The aqueous condensate (8) obtained in the intermediate coolings is discharged from the process. The compressed butadienic gas (9) is fed to an absorption stage which is operated with tetradecane as an absorbent. In the absorption stage, an inert gas stream (10) is removed from the $C_4$ hydrocarbon stream (11). The $C_4$ hydrocarbon stream (11) is separated in an extractive distillation stage into a stream (13) consisting substantially of butadiene and a stream (12) comprising n-butane and 2-butene. The stream (12) is fed to an isomerization stage, in which 2-butene is isomerized to 1-butene. The product gas mixture of the isomerization is separated by distillation into a product gas stream (15) comprising predominantly 1-butene and a recycle stream (14) which comprises predominantly n-butane and additionally 2-butene. The latter is recycled into the BDH.

The results of the simulation are shown in Table 2. The composition of the streams (1) to (15) is reported in parts by volume.

| Stream No. | 1 | 2 | 3 | 4 | 5 | 6 | 7 | 8 |
|---|---|---|---|---|---|---|---|---|
| Amount [kg/h] | 39060 | 28600 | 1832 | 77250 | 107682 | 67572 | 175254 | 18588 |
| Propane | 0.0000 | 0.0000 | 0.0000 | 0.0000 | 0.0065 | 0.0000 | 0.0037 | 0.0018 |
| Propene | 0.0000 | 0.0000 | 0.0000 | 0.0000 | 0.0000 | 0.0000 | 0.0000 | 0.0000 |
| Butane | 1.0000 | 0.0000 | 0.0000 | 0.9424 | 0.1848 | 0.0000 | 0.1053 | 0.0001 |
| 1-Butene | 0.0000 | 0.0000 | 0.0000 | 0.0000 | 0.0609 | 0.0000 | 0.0000 | 0.0000 |
| 2-Butene | 0.0000 | 0.0000 | 0.0000 | 0.0320 | 0.1307 | 0.0000 | 0.0479 | 0.0682 |
| 1,3-Butadiene | 0.0000 | 0.0000 | 0.0000 | 0.0000 | 0.0126 | 0.0000 | 0.0657 | 0.0002 |
| Water | 0.0000 | 0.0000 | 1.0000 | 0.0255 | 0.1434 | 0.0000 | 0.1498 | 0.9283 |
| Carbon dioxide | 0.0000 | 0.0000 | 0.0000 | 0.0000 | 0.0065 | 0.0000 | 0.0135 | 0.0011 |
| Hydrogen | 0.0000 | 0.2853 | 0.0000 | 0.0000 | 0.2230 | 0.0000 | 0.1268 | 0.0000 |
| Oxygen | 0.0000 | 0.1429 | 0.0000 | 0.0000 | 0.0000 | 0.2100 | 0.0400 | 0.0001 |
| N2 | 0.0000 | 0.5718 | 0.0000 | 0.0000 | 0.2315 | 0.7900 | 0.4473 | 0.0002 |
| Temperature [° C.] | 25.0 | 25.0 | 150.0 | 525.0 | 575.0 | 115.0 | 400.0 | 55.0 |
| Pressure [bar] | 3.1 | 3.1 | 3.1 | 3.1 | 2.7 | 2.7 | 2.4 | 10.2 |

| Stream No. | 9 | 10 | 11 | 12 | 13 | 14 | 15 |
|---|---|---|---|---|---|---|---|
| Amount [kg/h] | 156666 | 85434 | 71231 | 50481 | 20750 | 38190 | 12291 |
| Propane | 0.0041 | 0.0000 | 0.0155 | 0.0220 | 0.0000 | 0.0000 | 0.0584 |
| Propene | 0.0000 | 0.0000 | 0.0000 | 0.0000 | 0.0000 | 0.0000 | 0.0000 |
| Butane | 0.1243 | 0.0006 | 0.4750 | 0.6750 | 0.0000 | 0.9325 | 0.0536 |
| 1-Butene | 0.0000 | 0.0000 | 0.0000 | 0.0000 | 0.0000 | 0.0000 | 0.8193 |
| 2-Butene | 0.0442 | 0.0008 | 0.1675 | 0.2381 | 0.0000 | 0.0624 | 0.0000 |
| 1,3-Butadiene | 0.0776 | 0.0004 | 0.2963 | 0.0000 | 1.0000 | 0.0000 | 0.0000 |
| Water | 0.0091 | 0.0029 | 0.0267 | 0.0380 | 0.0000 | 0.0051 | 0.0000 |
| Carbon dioxide | 0.0157 | 0.0150 | 0.0176 | 0.0250 | 0.0000 | 0.0000 | 0.0662 |
| Hydrogen | 0.1497 | 0.2025 | 0.0000 | 0.0000 | 0.0000 | 0.0000 | 0.0000 |
| Oxygen | 0.0472 | 0.0635 | 0.0009 | 0.0013 | 0.0000 | 0.0000 | 0.0018 |
| N2 | 0.5281 | 0.7141 | 0.0004 | 0.0006 | 0.0000 | 0.0000 | 0.0007 |
| Temperature [° C.] | 55.0 | 35.0 | 85 | 40.0 | 40.0 | 40.0 | 40.0 |
| Pressure [bar] | 10.2 | 10.2 | 4.9 | 4.9 | 4.9 | 12.0 | 12.0 |

We claim:

1. A process for preparing butadiene from n-butane having the steps of

A) providing a feed gas stream a comprising n-butane;

B) feeding the feed gas stream a comprising n-butane into at least one first dehydrogenation zone and nonoxidatively catalytically dehydrogenating n-butane to obtain a product gas stream b comprising n-butane, 1-butene, 2-butene, butadiene, hydrogen, low-boiling secondary constituents and in some cases steam;

C) feeding the product gas stream b of the nonoxidative catalytic dehydrogenation and an oxygenous gas into at least one second dehydrogenation zone and oxidatively dehydrogenating n-butane, 1-butene and 2-butene to obtain a product gas stream c comprising n-butane, 2-butene, butadiene, low-boiling secondary constituents and steam, said product gas stream c having a higher content of butadiene than the product gas stream b;

D) removing the low-boiling secondary constituents and steam to obtain a $C_4$ product gas stream d substantially consisting of n-butane, 2-butene and butadiene;

E) separating the $C_4$ product gas stream d into a stream e1 consisting substantially of n-butane and 2-butene and a product of value stream e2 consisting substantially of butadiene by extractive distillation;

F) feeding the stream e1 consisting substantially of n-butane and 2-butene and a cycle stream g comprising 1-butene and 2-butene into a distillation zone and separating into a 1-butene-rich product of value stream f1, a recycle stream f2 comprising 2-butene and n-butane and a stream f3 comprising 2-butene, and recycling the recycle stream f2 into the first dehydrogenation zone;

G) feeding the stream f3 comprising 2-butene into an isomerization zone and isomerizing 2-butene to 1-butene to obtain a cycle stream g comprising 1-butene and 2-butene, and recycling the cycle gas stream g into the distillation zone.

2. The process according to claim 1, wherein the nonoxidative catalytic dehydrogenation of n-butane is carried out autothermally.

3. The process according to claim 1, wherein the feed stream a containing n-butane is obtained from liquefied petroleum gas (LPG).

4. The process according to claim 1, wherein the extractive distillation is carried out using N-methylpyrrolidone as an extractant.

5. The process according to claim 2, wherein the feed stream a containing n-butane is obtained from liquefied petroleum gas (LPG).

6. The process according to claim 2, wherein the extractive distillation is carried out using N-methylpyrrolidone as an extractant.

* * * * *